United States Patent [19]

Zink

[11] Patent Number: 5,066,814
[45] Date of Patent: Nov. 19, 1991

[54] 2-DICARBOXIMIDEFLUORANE OR 3-DICARBOXIMIDEFLUORANE COMPOUNDS

[75] Inventor: Rudolf Zink, Therwil, Switzerland

[73] Assignee: Ciba-Geigy Corporation, Ardsley, N.Y.

[21] Appl. No.: 485,355

[22] Filed: Feb. 23, 1990

[30] Foreign Application Priority Data

Feb. 24, 1989 [CH] Switzerland .................. 675/89

[51] Int. Cl.$^5$ .................................. C07D 493/10
[52] U.S. Cl. ............................ 548/407; 544/70; 546/15
[58] Field of Search ............... 544/70; 546/15; 548/407

[56] References Cited
FOREIGN PATENT DOCUMENTS
0266311 5/1988 European Pat. Off.

OTHER PUBLICATIONS
Zink, Chemical Abstracts, vol. 110 (1989) 145061u.

Primary Examiner—Richard L. Raymond
Attorney, Agent, or Firm—George R. Dohmann; Edward McC. Roberts

[57] ABSTRACT

2-Dicarboximidefluorane or 3-dicarboximidefluorane compounds of the formula

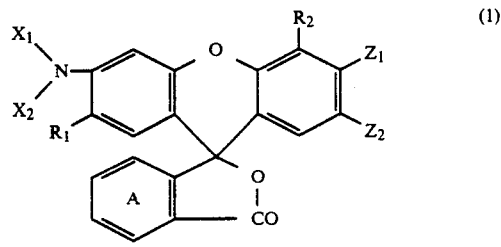

in which $R_1$ and $R_2$ independently of one another are each hydrogen, halogen, lower alkyl or lower alkoxy, one of $Z_1$ and $Z_2$ is the dicarboximide group

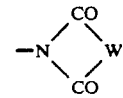

and the other is hydrogen, halogen, lower alkyl or lower alkoxy, W is a radical of a dicarboxylic acid containing at least 2 carbon atoms, $X_1$ and $X_2$ are hydrogen, alkyl which is unsubstituted or substituted by halogen, hydroxyl, cyano, tetrahydrofuryl or lower alkoxy, cycloalkyl, or benzyl or phenyl each of which is unsubstituted or substituted by halogen, cyano, nitro, lower alkyl, lower alkoxy, lower alkoxycarbonyl, —NX'X" or -4-NX'X"-phenylamino in which X' and X" independently of one another are hydrogen, lower alkyl, cyclohexyl, benzyl or phenyl, or $X_1$ and $X_2$, together with the nitrogen atom linking them, are a five-membered or six-membered heterocyclic radical and in which the ring A is unsubstituted or substituted by halogen, nitro, lower alkyl, lower alkoxy, lower alkylthio, lower alkoxycarbonyl, amino, mono-lower alkylamino or di-lower alkylamino.

These fluorane compounds, which are particularly fast to sublimation, are suitable for use as color formers in pressure-sensitive or heat-sensitive recording materials, and produce intense yellow, orange or red colorations which are fast to light.

13 Claims, No Drawings

2-DICARBOXIMIDEFLUORANE OR 3-DICARBOXIMIDEFLUORANE COMPOUNDS

The present invention relates to 2-dicarboximidefluorane or 3-dicarboximidefluorane compounds, a process for their preparation and their use as colour formers in pressure-sensitive or heat-sensitive recording materials.

The fluorane compounds according to the invention have the general formula

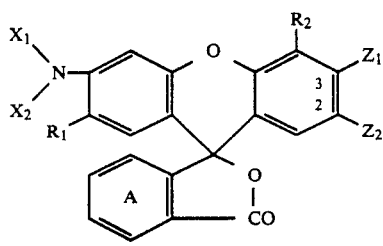

in which $R_1$ and $R_2$ independently of one another are each hydrogen, halogen, lower alkyl or lower alkoxy, one of $Z_1$ and $Z_2$ is the dicarboximide group

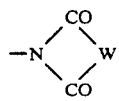

and the other is hydrogen, halogen, lower alkyl or lower alkoxy, W is a radical of a dicarboxylic acid containing at least 2 carbon atoms, $X_1$ and $X_2$ independently of one another are each hydrogen, alkyl which has not more than 12 carbon atoms and is unsubstituted or substituted by halogen, hydroxyl, cyano, tetrahydrofuryl or lower alkoxy, cycloalkyl which has 5 to 10 carbon atoms or benzyl or phenyl each of which is unsubstituted or substituted by halogen, cyano, nitro, lower alkyl, lower alkoxy, lower alkoxycarbonyl, —NX'X" or -4-NX'X"-phenylamino in which X' and X" independently of one another are hydrogen, lower alkyl, cyclohexyl, benzyl or phenyl, or $X_1$ and $X_2$, together with the nitrogen atom linking them, are a five-membered or six-membered heterocyclic radical which is preferably saturated, and in which the ring A is unsubstituted or substituted by halogen, nitro, lower alkyl, lower alkoxy, lower alkylthio, lower alkoxycarbonyl, amino, mono-lower alkylamino or di-lower alkylamino. The 2-dicarboximidefluoranes are preferred.

In the definition of the radicals of the fluorane compounds, lower alkyl, lower alkoxy and lower alkylthio are groups or constituents of groups containing 1 to 6, in particular 1 to 3, carbon atoms. Examples of groups of this type are methyl, ethyl, n-propyl, isopropyl, n-butyl, sec-butyl, tert-butyl, amyl, isoamyl, tert-amyl, hexyl, methoxy, ethoxy, isopropoxy, isobutoxy or tert-butoxy or methylthio, ethylthio, propylthio or butylthio, respectively.

Halogen is, for example, fluorine, bromine or preferably chlorine.

In the imide group W is, for example, a divalent, aliphatic, cycloaliphatic or aromatic radical which is attached to the carboxyl groups of the imide grouping.

When it is a divalent, aliphatic radical, W is advantageously a linear or branched hydrocarbon radical of a saturated or ethylenically unsaturated dicarboxylic acid which has 4 to 10 carbon atoms and is unsubstituted or substituted by halogen. Examples of suitable aliphatic, saturated dicarboxylic acids of this type are succinic or glutaric acid. Ethylenically unsaturated dicarboxylic acids are preferably maleic, dimethylmaleic, dichloromaleic, itaconic, citraconic or glutaconic acid.

When W is a divalent, cycloaliphatic radical, it is, in particular, the radical of a tetrahydrophthalic or hexahydrophthalic acid.

W is preferably the divalent radical of an aromatic dicarboxylic acid, for example a naphthalenedicarboxylic acid or an o-phthalic acid.

W is preferably a phenylene radical which can be substituted by nitro, halogen, for example chlorine or bromine, lower alkyl, lower alkoxy or lower alkoxycarbonyl. In particular, W is an unsubstituted phenylene radical.

$R_1$ and $R_2$ and also one Z are preferably hydrogen, methyl, methoxy or chlorine.

If the radicals $X_1$ and $X_2$ are alkyl groups, they can be linear or branched. Examples of such alkyl radicals are methyl, ethyl, n-propyl, isopropyl, n-butyl, sec-butyl, tert-butyl, 1,1,3,3-tetramethylbutyl, amyl, isoamyl, n-hexyl, 2-ethylhexyl, n-heptyl, n-octyl, isooctyl, n-nonyl, isononyl or n-dodecyl.

If the alkyl radicals in $X_1$ and $X_2$ are substituted, this substituent is, in particular, cyanoalkyl, halogenoalkyl, hydroxyalkyl or alkoxyalkyl preferably having in each case a total of 2 to 8 carbon atoms, for example β-cyanoethyl, β-chloroethyl, γ-chloropropyl, β-hydroxyethyl, γ-hydroxypropyl, β-methoxyethyl, β-ethoxyethyl or γ-methoxypropyl. Another substituted alkyl radical is tetrahydrofurfuryl.

Examples of X radicals as cycloalkyl are cylopentyl, cycloheptyl or preferably cyclohexyl. The cycloalkyl radicals can contain one or more $C_1$–$C_4$alkyl radicals, preferably methyl groups, and have a total of 5 to 10 carbon atoms.

Examples of preferred substituents in the benzyl and phenyl group of the X radicals are halogen, cyano, methyl, methoxy or carbomethoxy. Examples of araliphatic or aromatic radicals of this type are methylbenzyl, 2,4-dimethylbenzyl, 2,5-dimethylbenzyl, chlorobenzyl, dichlorobenzyl, cyanobenzyl, tolyl, xylyl, 2,6-dimethylphenyl, chlorophenyl, methoxyphenyl or carbomethoxyphenyl.

If the substituents ($X_1$ and $X_2$), together with the common nitrogen atom, are a heterocyclic radical, this is, for example, pyrrolidino, piperidino, pipecolino, morpholino, thiomorpholino or piperazino, for example N-methylpiperazino. Preferred saturated heterocyclic radicals for -$NX_1X_2$ are pyrrolidino, piperidino or morpholino.

The substituents $X_1$ and $X_2$ are preferably cyclohexyl, tolyl, xylyl, benzyl, cyano-lower alkyl, for example β-cyanoethyl, or primarily lower alkyl, for example methyl, ethyl, n-propyl, isopropyl, n-butyl, amyl, hexyl. —$NX_1X_2$ is preferably also pyrrolidinyl, N-lower alkyl-N-tetrahydrofurfurylamino, 4-di-lower alkylamino-phenylamino or 4-(4'-phenylaminophenylamino)-phenylamino.

The ring A can advantageously contain, as a substituent, halogen, nitro, lower alkyl, lower alkoxy or di-lower alkylamino. The benzene ring A is preferably unsubstituted or substituted by 1 to 4 halogen atoms.

Dicarboximide fluorane compounds of practical importance have the formula

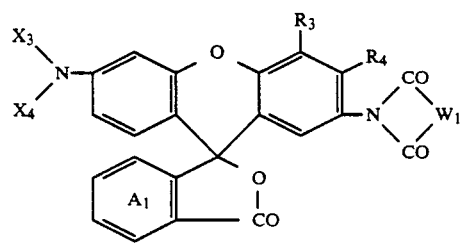

or the formula

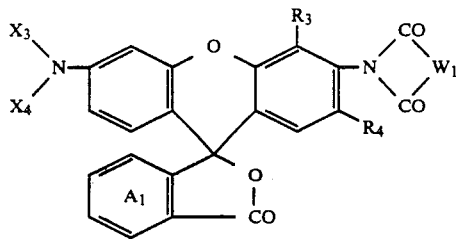

in which $W_1$ is alkylene or alkenylene having 2 to 4 carbon atoms, cyclohexylene or phenylene which is unsubstituted or substituted by halogen, for example chlorine or bromine, methyl, methoxy or carbomethoxy, $R_3$ and $R_4$ independently of one another are each hydrogen, halogen or lower alkyl, $X_3$ is $C_1$-$C_6$alkyl, $C_5$-$C_6$cycloalkyl, benzyl, phenyl or phenyl which is substituted by halogen, $C_1$-$C_4$alkyl or $C_1$-$C_4$alkoxy, $X_4$ is $C_1$-$C_6$alkyl or benzyl or —$NX_3X_4$ is pyrrolidinyl, piperidinyl, morpholinyl or N-lower alkyl-N-tetrahydrofurfurylamino and in which the benzene ring $A_1$ is unsubstituted or is substituted by halogen, lower alkyl or lower alkoxy.

Amongst the compounds of the formulae (2) and (3), the fluorane compounds in which $W_1$ is phenylene which is unsubstituted or substituted by chlorine, $X_3$ and $X_4$ are $C_1$-$C_4$alkyl, $R_3$ and $R_4$ are hydrogen, methyl or chlorine and the ring $A_1$ is unsubstituted are preferred.

Fluorane compounds of particular interest are those of the formula

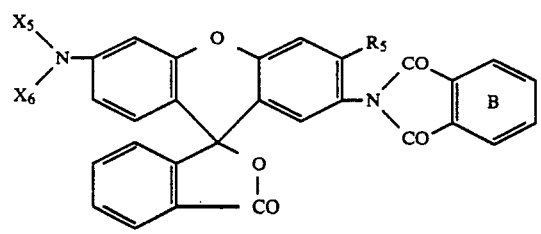

in which $R_5$ is hydrogen or methyl, $X_5$ is $C_1$-$C_4$alkyl, cyclohexyl or tolyl and $X_6$ is $C_1$-$C_4$alkyl and the ring B is unsubstituted or substituted by 1 to 4 chlorine atoms.

The fluorane compounds, according to the invention, of the formulae (1) to (4) are prepared by reacting a keto-acid compound of the formula

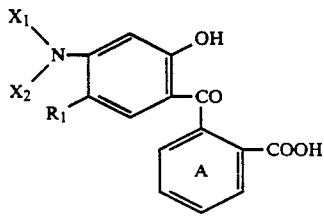

in which A, $X_1$, $X_2$ and $R_1$ are as defined with a compound, containing the imide, of the formula

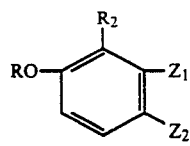

group in which $R_2$, $Z_1$ and $Z_2$ are as defined and R is hydrogen or methyl.

The reaction is preferably carried out in such a way that the reactants are caused to react in the presence of an acid condensation agent at a temperature of 20° to 140° C. Examples of condensation agents of this type are acetic anhydride, zinc chloride, aluminium chloride, sulfuric acid, phosphoric acid and phosphorusoxy chloride.

The end product of the formula (1) is isolated in a generally known manner by adjusting the pH of the reaction mixture to a value of at least 6, preferably 7 to 14, for example by means of alkalis, for example alkali metal hydroxides, ammonia or alkali metal carbonates or bicarbonates and separating off the product formed and washing and drying it, or by treatment with suitable organic solvents, for example methanol, isopropanol, benzene, chlorobenzene, toluene or xylene. If necessary, petroleum ether, water or aqueous ammonia can also be used concomitantly to recrystallize the fluorane compounds.

The starting materials of the formulae (5) and (6) are for the most part known.

In an alternative process the fluorane compounds, according to the invention, of the formulae (1) to (4) can be prepared by reacting an aminofluorane compound of the formula

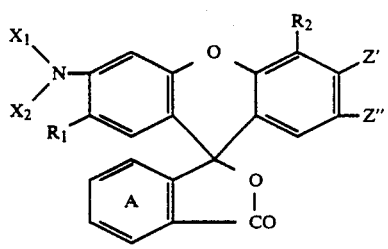

in which one of Z' and Z" is -$NH_2$ and the other is hydrogen, halogen, lower alkyl or lower alkoxy and $R_1$, $R_2$, $X_1$, $X_2$ and A are as defined with a dicarboxylic anhydride of the formula

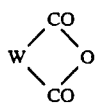

$$\begin{matrix} & CO \\ & / \quad \backslash \\ W & \quad O \\ & \backslash \quad / \\ & CO \end{matrix} \qquad (8)$$

in which W is as defined.

Specific examples of anhydride components of the formula (8) are succinic anhydride, glutaric anhydride, maleic anhydride, dimethylmaleic anhydride, dichloromaleic anhydride, citraconic anhydride, itaconic anhydride, phthalic anhydride, tetrachlorophthalic anhydride, 1,8-naphthalic anhydride or 1,4,5,6,7,7-hexachloro-5-norbornene-2,3-dicarboxylic anhydride.

The reaction of the fluorane compound of the formula (7) with the dicarboxylic anhydride compound of the formula (8) can be carried out at a temperature of 10° to 140° C. The reaction medium used can be an organic solvent and/or a lower aliphatic carboxylic acid, for example acetic acid.

Examples of suitable solvents are cycloaliphatic or aromatic hydrocarbons, for example cyclohexane, benzene, toluene or xylene; chlorinated hydrocarbons, such as chloroform, ethylene chloride or chlorobenzene; ethers, such as diethyl ether or glycol dimethylether; cyclic ethers, such as dioxane or tetrahydrofuran; and also dimethylformamide, diethylformamide, dimethyl sulfoxide or acetonitrile.

The fluorane compounds of the formulae (1) to (4) are normally colourless or at the most slightly coloured. When these colour formers are brought into contact with a developer, preferably an acid developer, i.e. an electron acceptor, they produce in most cases intensely yellow, orange or red colour shades which are particularly fast to light.

The fluorane compounds of the formulae (1) to (4) are also very valuable when mixed with one or more other known colour formers, for example 3,3-(bisaminophenyl)-phthalides, 3-indolyl-3-aminophenylazaphthalides, (3,3-bisindolyl)-phthalides, 3-aminofluoranes, 6-dialkylamino-2-dibenzylaminofluoranes, 6-dialkylamino-3-methyl-2-arylaminofluoranes, 3,6-bisalkoxyfluoranes, leucoauramines, spiropyranes, spirodipyranes, chromenopyrazoles, chromenoindoles, phenoxazines, phenothiazines, quinazolines, rhodamine lactams, carbazolylmethanes or other triarylmethane leuco dyes, in order to obtain grey or black colorations.

The fluorane compounds of the formulae (1) to (4) also exhibit an excellent colour intensity both on activated clays and on phenolic substrates. They are particularly suitable for use as rapidly developing colour formers for use in a heat-sensitive or, in particular, pressure-sensitive recording material, which can be either a copying material or a registering material. They are distinguished by the fact that they are stable to pH and are readily soluble in the capsule oils. After exposure in a CB sheet they exhibit a slight decrease in tinctorial strength (CB deactivation). Their fastness to sublimation is excellent.

A pressure-sensitive material consists, for example, of at least one pair of sheets containing at least one colour former of the formulae (1) to (4) dissolved in an organic solvent, and an electron acceptor as developer.

Typical examples of developers of this type are activated clay substances, for example attapulgite clay, acid clay, bentonite, montmorillonite, activated clay, for example acid-activated bentonite or montmorillonite, and also zeolite, halloysite, silicon dioxide, aluminium oxide, aluminium sulfate, aluminium phosphate, zinc chloride, zinc nitrate, zirconium dioxide, activated kaolin or any desired type of clay. Developers which can also be used are organic compounds having an acid reaction, for example phenols, resorcinols or salicylic acids which are unsubstituted or substituted in the ring, for example 3,5-bis-($\alpha,\alpha$-dimethylbenzyl)-salicylic acid or 3,5-bis-($\alpha$-methylbenzyl)-salicylic acid or salicylic acid esters, and metal salts thereof, for example zinc salts, and also a polymeric material having an acid reaction, for example a phenolic polymer, an alkylphenolacetylene resin, a maleic acid/colophony resin or a partly or completely hydrolysed polymer of maleic anhydride with styrene, ethylene or vinylmethylether, or carboxymethylene. It is also possible to employ mixtures of the monomeric and polymeric compounds mentioned. Developers which are particularly preferred are acid-activated bentonite, zinc salicylates or the condensation products of p-substituted phenols with formaldehyde. The latter can also be modified with zinc.

The developers can, in addition, also be employed as a mixture with pigments or other adjuncts which in themselves are unreactive or of low reactivity, such as silica gel or UV absorbers, for example 2-(2'-hydroxyphenyl)-benzotriazoles. The following are examples of pigments of this type: talc, titanium dioxide, aluminium oxide, aluminium hydroxide, zinc oxide, chalk, clays, such as kaolin, and organic pigments, for example urea-formaldehyde condensates (BET surface area 2–75 m$^2$/g) or melamine-formaldehyde condensation products.

At the points where it comes into contact with the electron acceptor, the colour former produces a coloured marking. In order to prevent premature activation of the colour formers present in the pressure-sensitive recording material, these are as a rule separated from the electron acceptor. This can preferably be achieved by incorporating the colour formers in foam-like, sponge-like or honeycomb-like structures. Preferably the colour formers are enclosed in microcapsules which, as a rule, can be ruptured by pressure. When the capsules are ruptured by pressure, for example by means of a pencil, the colour former solution is transferred onto an adjacent sheet coated with an electron acceptor, as the result of which a coloured place is produced. The colour results from the dyestuff formed in the course of this, which absorbs within the visible range of the electromagnetic spectrum.

The colour formers are preferably encapsulated in the form of solutions in organic solvents. Examples of suitable solvents are, preferably, non-volatile solvents, for example halogenated benzene, biphenyl or paraffin, such as chloroparaffin, trichlorobenzene, monochlorobiphenyl, dichlorobiphenyl or trichlorobiphenyl; esters, for example tricresylphosphate, di-n-butylphthalate, dioctylphthalate or trichloroethyl phosphate; aromatic ethers, such as benzylphenylether, hydrocarbon oils, such as paraffin or kerosine, for example derivatives of biphenyl, naphthalene or terphenyl alkylated by isopropyl, isobutyl, sec-butyl or tert-butyl, dibenzyltoluene, partially hydrogenated terphenyl, mono-$C_1$-$C_3$alkylated to tetra-$C_1$-$C_3$alkylated diphenylalkanes, dodecylbenzene, benzylated xylenes or other chlorinated or hydrogenated, condensed aromatic hydrocarbons. Mixtures of different solvents, in particular mixtures of paraffin oils or kerosine and diisopropylnaphthalene or partially hydrogenated terphenyl are often employed in order to obtain an optimum solubility for the formation of colour, a rapid and intense coloration and a viscosity favourable for the micro-encapsulation. In regard to encapsulation, the fluorane compounds according to the invention are distinguished by the fact that they exhibit an extremely high stability to pH, for example within a pH range from 4 to 10.

The capsule walls are formed uniformly by coaservation forces around the droplets of the colour former solution, the encapsulating material being described, for example, in U.S. Pat. No. 2,800,457. The capsules can preferably also be formed from an aminoplast or modified aminoplasts by polycondensation, as described in British Patent Specifications 989,264, 1,156,725, 1,301,052 and 1,355,124. Microcapsules which are formed by interface polymerization, for example capsules composed of polyester, polycarbonate, polysulfonamide, polysulfonate but particularly polyamide or polyurethane are also suitable.

The microcapsules containing colour formers of the formulae (1) to (4) can be used for the production of pressure-sensitive copying materials of a very wide variety of known types. The various systems differ essentially from one another in the arrangement of the capsules, the colour reactants and the carrier material.

A preferred arrangement is one in which the encapsulated colour formers are present in the form of a layer on the reverse side of a transfer sheet, and the electron acceptor is present in the form of a layer on the front side of a receiver sheet. Another arrangement of the constituents consists in the microcapsules containing the colour former, and the developer being present in or on the same sheet in the form of one or more individual layers or being present in the paper pulp.

The capsules are preferably attached to the carrier by means of a suitable binder. Since paper is the preferred carrier material, this binder is mainly paper coating agents, such as gum arabic, polyvinyl alcohol, hydroxymethyl cellulose, casein, methyl cellulose, dextrin, starch, starch derivatives or polymer lattices. Examples of the latter are butadiene/styrene copolymers or acrylic homopolymers or copolymers.

The paper used is not only normal paper composed of cellulose fibres, but also paper in which the cellulose fibres have been replaced (partly or wholly) by fibres composed of synthetic polymers. The layer carrier can also be a plastic film.

The duplicating material is also preferably so constituted that it contains a capsule-free layer containing the colour former and a colour-developing layer containing, as colour developer, at least one inorganic metal salt of a polyvalent metal, in particular halides or nitrates, for example zinc chloride, tin chloride, zinc nitrate or mixtures thereof.

The compounds of the formulae (1) to (4) can also be used as colour formers in a heat-reactive recording material. This contains, as a rule, at least one layer carrier, one or more colour formers, an electron acceptor and, if appropriate, also a binder and/or wax. If desired, it is also possible for activators or sensitizers to be present in the recording material.

Heat-reactive recording systems embrace, for example, heat-sensitive recording materials and paper and copying materials and paper. These systems are used, for example, for recording information, for example in electronic computers, teleprinters, teletypers or recording instruments and measuring instruments, for example electrocardiographs. The production of an image (marking) can also be carried out manually by means of a heated pen. Laser beams are a further device for the production of markings by means of heat.

The heat-reactive recording material can also be so composed that the colour former is dissolved or dispersed in a binder layer, and the developer is dissolved and dispersed in the binder in a second layer. Another possibility consists in both the colour former and the developer being dispersed in one layer. The layer or layers are softened in specific areas by means of heat, where upon the desired colour develops immediately in the heated sections.

The same electron acceptors such as are used in pressure-sensitive paper are suitable as developers. Examples of developers are the clay minerals and phenolic resins already mentioned, or phenolic compounds such as are described, for example, in German Patent Specification 1,251,348, for example 4-tert-butylphenol, 4-phenylphenol, methylenebis-(p-phenylphenol), 4-hydroxydiphenyl ether, α-naphthol, β-naphthol, methyl or benzyl 4-hydroxybenzoate, 4-hydroxydiphenyl sulfone, 2,4-dihydroxydiphenyl sulfone, 4'-hydroxy-4-methyldiphenyl sulfone, 4'-hydroxy-4-isopropoxydiphenyl sulfone, 4-hydroxyacetophenone, 2,2'-dihydroxybiphenyl, 4,4'-cyclohexylidenediphenol, 4,4'-isopropylidenediphenol, 4,4'-isopropylidenebis-(2-methylphenol), an antipyrine complex of zinc thiocyanate, a pyridine complex of zinc thiocyanate, a cresidine complex of zinc thiocyanate, 4,4-bis-(4-hydroxyphenyl)-valeric acid, hydroquinone, pyrogallol, phloroglucinol, p-, m- or o-hydroxybenzoic acid, gallic acid, 1-hydroxy-2-naphthoic acid, hydroxyphthalic acid and boric acid or organic, preferably aliphatic, dicarboxylic acids, for example tartaric acid, oxalic acid, maleic acid, citric acid, citraconic acid or succinic acid.

It is preferable to use fusible, film-forming binders for the preparation of the heat-reactive recording material. These binders are normally water-soluble, whereas the fluorane compounds and the developer are sparingly soluble or insoluble in water. The binder should be capable of dispersing and fixing the colour former and the developer at room temperature.

Examples of binders which are water-soluble or at least swellable in water are hydrophillic polymers, such as polyvinyl alcohol, polyacrylic acid, hydroxyethyl cellulose, methyl cellulose, carboxymethyl cellulose, polyacrylamide, polyvinylpyrrolidone, carboxylated butadiene/styrene copolymers, gelatin, starch or etherified maize starch.

If the colour former and the developer are present in two separate layers, it is possible to use binders insoluble in water, i.e. binders soluble in non-polar or only weakly polar solvents, for example natural rubber, synthetic rubber, chlorinated rubber, polystyrene, styrene/butadiene copolymers, polymethyl acrylates, ethyl cellulose, nitrocellulose and polyvinylcarbazole. However, the preferred arrangement is that in which the colour former and the developer are present in a water-soluble binder in one layer.

The material can also be provided with an additional protective layer in order to ensure the stability of the heat-sensitive recording material or the image density of the developed image. Protective layers of this type as a rule consist of water-soluble and/or water-insoluble resins which are conventional polymer materials or aqueous emulsions of these polymer materials.

Both the heat-reactive layers and the resin layers can contain further additives. In order to improve the degree of whiteness, to facilitate the printing of the papers and to prevent the heated pen from sticking, these layers can contain, for example, talc, titanium dioxide, zinc oxide, aluminium hydroxide, calcium carbonate (for example chalks), magnesium carbonate, clays or organic pigments, for example urea/formaldehyde polymers. Substances such as urea, thiourea, diphenylthiourea, acetamide, acetanilide, benzenesulfanilide, bis-stearoylethylenediamide, stearamide, phthalic anhydride, metal stearates, for example zinc stearate, phthalonitrile, benzylbiphenyl, dimethyl terephthalate, dibenzylterephthalate or other corresponding fusible products which induce simultaneous melting of the colour former and the developer can be added to ensure that the colour is formed only within a limited temperature range. Thermographic recording materials preferably contain waxes, for example carnauba wax, montan wax, paraffin wax, polyethylene wax, condensates of higher fatty acid amides and formaldehyde or condensates of higher fatty acids and ethylenediamine.

A further application of the compounds of the formulae (1) to (4) is the production of a colour image by means of photo-curable microcapsules, as described, for example in German Offenlegungsschrift 3,247,488.

In the following examples the percentages indicated are by weight, unless stated otherwise. Parts are parts by weight.

EXAMPLE 1

7.8 g of 2'-carboxy-2-hydroxy-4-diethylaminobenzophenone are dissolved in 55 g of 100% sulfuric acid at 10° C. 6.3 g of N-(4-methoxyphenyl)-phthalimide are introduced at 5°-10° C. in the course of 20 minutes, and the mixture is stirred for 1 hour at 20°-22° C. The resulting solution is poured into 250 ml of ice water, the resulting suspension is filtered at 22° C. after 1 hour and the material on the filter is washed with cold water. 50 g of the material on the filter are suspended in 100 ml of toluene together with 6.9 g of finely ground potassium carbonate. The mixture is heated to reflux temperature (82° C.) and the water is removed from the system by means of a water separator in the course of 2 hours, the reflux temperature rising to 105° C. The toluene phase is then extracted several times with water and is clarified by filtration. 9 g of the fluorane compound of the formula

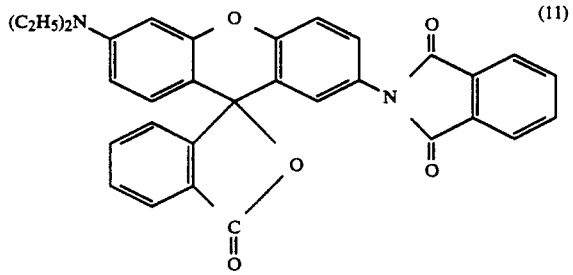

are obtained by concentration in the form of yellowish crystals, melting point: 221°-222° C.

This colour former is distinguished by good fastness to sublimation and it immediately develops a red colour on activated clay.

EXAMPLE 2

The procedure of Example 1 is repeated, except that 6.7 g of N-(4-methoxy-2-methylphenyl)-phthalimide are employed instead of 6.3 g of N-(4-methoxyphenyl)-phthalimide, affording the fluorane compound of the formula

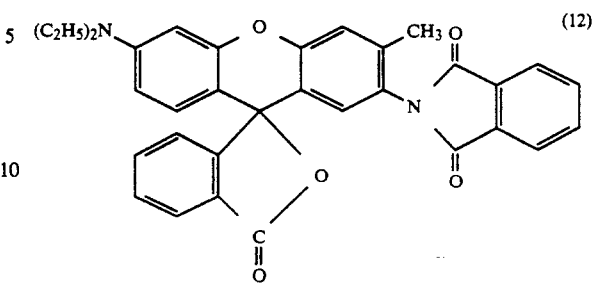

having a melting point of 260°-262° C. This sublimation-fast colour former immediately develops an orange colour on activated clay.

EXAMPLE 3

7.7 g of 2-amino-6-diethylaminofluorane are dissolved at 25° C. in 75 ml of glacial acetic acid. 5.7 g of tetrachlorophthalic anhydride are introduced with good stirring in the course of 15 minutes, the temperature rising to 32° C. The mixture is heated to 80° C. and kept at this temperature for 10 minutes. The cyclization to give the imide is monitored by means of thin layer chromatography. The reaction solution is cooled slowly with stirring, in the course of which the product crystallizes out starting at 75° C. After 3 hours the mixture is filtered at 25° C. and the material on the filter is washed with 1 l of distilled water. After drying, 12.2 g of a fluorane compound of the formula

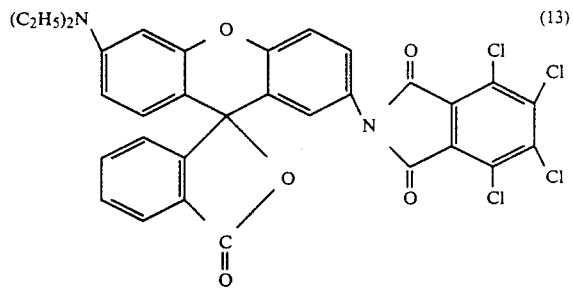

are obtained. The pure product of melting point 285°-287° C. is obtained by recrystallization from xylene (mixture of isomers). An instant, red colour is produced on activated clay by means of this compound.

EXAMPLE 4

27.7 g of 2'-carboxy-2-hydroxy-4-n-dibutylaminobenzophenone are dissolved at 45° C. in 150 g of sulfuric acid monohydrate. 19 g of N-(4-methoxyphenyl)-phthalimide are introduced at 5°-10° C. in the course of 15 minutes and the mixture is first stirred for 1 hour at 0°-10° C., warmed to 25° C. and then stirred for a further hour at 25°-30° C. The resulting solution is discharged into 750 ml of ice water, in the course of which the product is precipitated. The resulting suspension is stirred for a further 15 hours at 20°-25° C., the pH is adjusted with 40% sodium hydroxide solution to a value of 10, the temperature also being adjusted to 55° C., and the mixture is stirred for a further hour under these conditions and filtered.

The moist product obtained is introduced into a mixture of 150 ml of xylene (mixture of isomers) and 13.8 g of potassium carbonate, the mixture is heated to the boil and water is distilled off azeotropically until a boiling point of 122° C. is reached. The mixture is worked up by adding 200 ml of water, separating the xylene phase and concentrating it to dryness. This gives 26.4 g of a compound of the formula

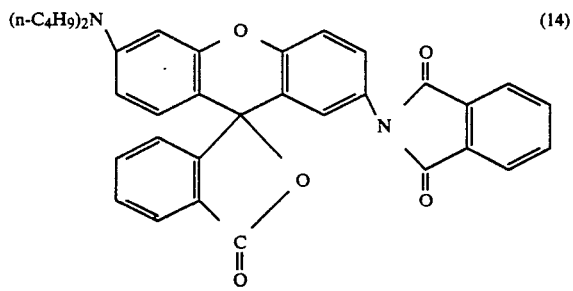

which, after recrystallization from 3 parts of toluene and 1 part of petroleum ether, is precipitated in a pure form having a melting point of 101°-104° C.

This colour former is very readily soluble in capsule oil, shows no tendency at all to sublime and immediately develops a red colour on zinc salicylate.

EXAMPLE 5

15.6 g of 2'-carboxy-2-hydroxy-4-diethylaminobenzophenone are dissolved at 40° C. in 110 g of 96% sulfuric acid. 12.6 g of N-(3-methoxyphenyl)-phthalimide are introduced at 5°-10° C. in the course of 45 minutes, the temperature is raisedo 20° C. in the course of 30 minutes and the mixture is poured into 500 ml of ice water. The suspension is stirred for a further hour at 20° C. and is then filtered, after which the phthalide compound obtained (28.8 g) is washed and dried.

The phthalide compound is then cyclized to the fluorane by being suspended in 100 ml of xylene (mixture of isomers) and 13.8 ml of triethylamine, and heated to reflux temperature (115° C.). The mixture is kept for 4 hours, in the course of which the reflux temperature falls to 105° C. The mixture is cooled to 20° C., water is added and the xylene phase is separated off and concentrated to dryness. This gives 25.8 g of compound of the formula

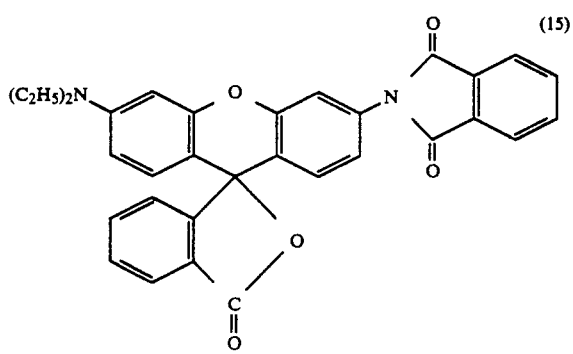

which, after recrystallization from toluene, has a melting point of 218°-220° C. This colour former is fast to sublimation and immediately develops a red colour with very good fastness to light on phenolic resin CF.

EXAMPLE 6

PREPARATION OF PRESSURE-SENSITIVE COPYING PAPER

A solution of 1 g of the fluorane compound of the formula (13)(Example 3) in 80 g of diisopropylnaphthalene and 19 g of kerosine is microencapsulated by coaservation in a manner known per se by means of gelatin and gum arabic, mixed with starch solution and used to coat a sheet of paper. A second sheet of paper is coated on its front side with activated clay as a colour developer. The first sheet of paper, containing the sublimation-fast colour former, and the sheet of paper coated with the colour developer are laid on top of one another with the coatings adjacent. Pressure is exerted on the first sheet by handwriting or typing, and an intense red copy, which has excellent fastness to light, is immediately developed on the sheet coated with the developer.

EXAMPLE 7

Example 6 is repeated, except that the fluorane compound of the formula (13) is replaced by a mixture of 1 g of the fluorane compound of the formula (12), 0.8 g of 3,3-bis-(4'-dimethylaminophenyl)-6-dimethylaminophthalide, 0.8 g of N-butylcarbazol-3-yl-bis-(4'-N-methyl-N-phenylaminophenyl)methane and 2.4 g of 6-diethylamino-2-dibenzylaminofluorane, the procedure being otherwise as described in Example 6, affording a pressure-sensitive recording material which produces an intense, light-fast, black copy by handwriting or by typing.

EXAMPLE 8

1 g of the fluorane compound of the formula (11) according to Example 1 is dissolved in 17 g of toluene. 12 g of polyvinyl acetate, 8 g of calcium carbonate and 2 g of titanium dioxide are added to this solution with stirring. The resulting suspension is diluted with toluene in a ration of 1:1 by weight and is used to coat a sheet of paper by means of a 10 μm doctor-blade. A second sheet of paper the underside of which is coated at a coating weight of 3 g/m² with a mixture consisting of 1 part of an amide wax, 1 part of a stearin wax and 1 part of zinc chloride is laid on the first sheet of paper. Pressure is exerted on the upper sheet by handwriting or typing, and an intense, red-orange colour is immediately developed on the sheet coated with the colour former.

EXAMPLE 9

PREPARATION OF A HEAT-SENSITIVE RECORDING MATERIAL 32 g of 4,4'-isopropylidenediphenol (Bisphenol A), 3.8 g of the distearamide of ethylenediamine, 39 g of kaolin, 20 g of an 88% hydrolysed polyvinyl alcohol and 500 ml of water are ground in a bore mill until the particle size is approx. 5 μm. 6 g of the fluorane compound of the formula (12) according to Example 2,3 g of an 88% hydrolysed polyvinyl alcohol and 60 ml of water are ground in a second bore mill to a particle size of approx. 3 μm.

The two dispersions are combined and are used to coat a sheet of paper at a dry coating weight of 5.5 g/m². An intense, light-fast, orange colour is obtained by touching the sheet of paper with a heated metal pin.

What is claimed is:

1. A 2-dicarboximidefluorane or 3-dicarboximidefluorane compound of the formula

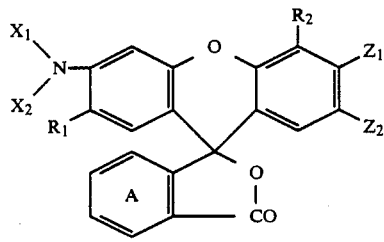

(1)

in which $R_1$ and $R_2$ independently of one another are each hydrogen, halogen, lower alkyl or lower alkoxy, one of $Z_1$ and $Z_2$ is the dicarboximide group

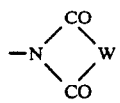

and the other is hydrogen, halogen, lower alkyl or lower alkoxy, W is a radical of a dicarboxylic acid containing at least 2 carbon atoms, $X_1$ and $X_2$ independently of one another are each hydrogen, alkyl which has not more than 12 carbon atoms and is unsubstituted or substituted by halogen, hydroxyl, cyano, tetrahydrofuryl or lower alkoxy, cycloalkyl which has 5 to 10 carbon atoms or benzyl or phenyl each of which is unsubstituted or substituted by halogen, cyano, nitro, lower alkyl, lower alkoxy, lower alkoxycarbonyl, —NX'X" or -4-NX'X"-phenylamino in which X' and X" independently of one another are hydrogen, lower alkyl, cyclohexyl, benzyl or phenyl, or $X_1$ and $X_2$, together with the nitrogen atom linking them, are a five-membered or six-membered heterocyclic radical, and in which the ring A is unsubstituted or substituted by halogen, nitro, lower alkyl, lower alkoxy, lower alkylthio, lower alkoxycarbonyl, amino, mono-lower alkylamino or di-lower alkylamino.

2. A fluorane compound according to claim 1, wherein $R_1$, $R_2$ and one Z in formula (1) independently of one another are each hydrogen, methyl, methoxy or chlorine.

3. A fluorane compound according to claim 1, wherein $X_1$ and $X_2$ in formula (1) independently of one another are lower alkyl, cyclohexyl, tolyl, benzyl or cyano-lower alkyl, or —$NX_1X_2$ is pyrrolidinyl, N-lower alkyl tetrahydrofurfurylamino, 4-di-lower alkylaminophenylamino or 4-(4'-phenylamino-phenylamino)-phenylamino.

4. A fluorane compound according to claim 1, wherein W in formula (1) is a linear or branched hydrocarbon radical of a saturated or ethylenically unsaturated dicarboxylic acid having 4 to 10 carbon atoms, which is unsubstituted or substituted by halogen.

5. A fluorane compound according to claim 1, wherein W in formula (1) is the divalent radical of a tetrahydrophthalic acid, hexahydrophthalic acid, phthalic acid or naphthalenedicarboxylic acid.

6. A fluorane compound according to claim 1, wherein W in formula (1) is a phenylene radical which is unsubstituted or substituted by halogen, nitro, lower alkyl, lower alkoxy or lower alkoxycarbonyl.

7. A fluorane compound according to claim 1, wherein the ring A in formula (1) is unsubstituted or substituted by halogen, nitro, lower alkyl, lower alkoxy or di-lower alkylamino.

8. A fluorane compound according to claim 1, which has the formula

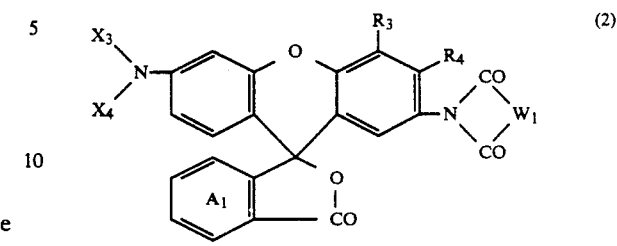

(2)

in which $W_1$ is alkylene or alkenylene having 2 to 4 carbon atoms, cyclohexylene or phenylene which is unsubstituted or substituted by halogen, methyl, methoxy or carbomethoxy, $R_3$ and $R_4$ independently of one another are each hydrogen, halogen or lower alkyl, $X_3$ is $C_1$-$C_6$alkyl, $C_5$-$C_6$cycloalkyl, benzyl, phenyl or phenyl which is substituted by halogen, $C_1$-$C_4$alkyl or $C_1$-$C_4$alkoxy, $X_4$ is $C_1$-$C_6$alkyl or benzyl or —$NX_3X_4$ is pyrrolidinyl, piperidinyl, morpholinyl or N-lower alkyl-N-tetrahydrofurfurylamino and in which the benzene ring $A_1$ is unsubstituted or is substituted by halogen, lower alkyl or lower alkoxy.

9. A fluorane compound according to claim 8, wherein in formula (2), $W_1$ is phenylene which is unsubstituted or substituted by chlorine, $X_3$ and $X_4$ are $C_1$-$C_4$alkyl, $R_3$ and $R_4$ are hydrogen, methyl or chlorine and the ring $A_1$ is unsubstituted.

10. A fluorane compound according to claim 1, which has the formula

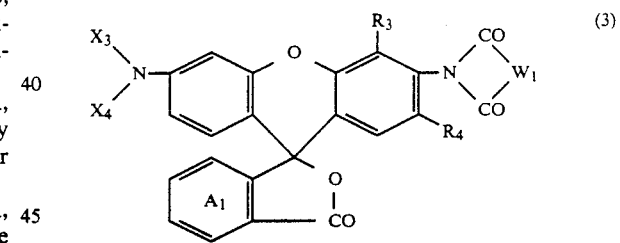

(3)

in which $W_1$ is alkylene or alkenylene having 2 to 4 carbon atoms, cyclohexylene or phenylene which is unsubstituted or substituted by halogen, methyl, methoxy or carbomethoxy, $R_3$ and $R_4$ independently of one another are each hydrogen, halogen or lower alkyl, $X_3$ is $C_1$-$C_6$alkyl, $C_5$-$C_6$cycloalkyl, benzyl, phenyl or phenyl which is substituted by halogen, $C_1$-$C_4$alkyl or $C_1$-$C_4$alkoxy, $X_4$ is $C_1$-$C_6$alkyl or benzyl or —$NX_3X_4$ is pyrrolidinyl, piperidinyl, morpholinyl or N-lower alkyl-N-tetrahydrofurfurylamino and in which the benzene ring $A_1$ is unsubstituted or is substituted by halogen, lower alkyl or lower alkoxy.

11. A fluorane compound according to claim 10 wherein, in formula (3), $W_1$ is phenylene which is unsubstituted or substituted by chlorine, $X_3$ and $X_4$ are $C_1$-$C_4$alkyl, $R_3$ and $R_4$ are hydrogen, methyl or chlorine and the ring $A_1$ is unsubstituted.

12. A fluorane compound according to claim 1, which has the formula (4) 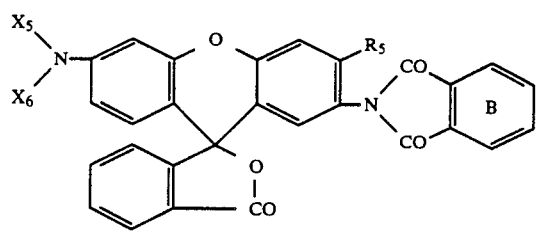
in which $R_5$ is hydrogen or methyl, $X_5$ is $C_1$-$C_4$alkyl, cyclohexyl or tolyl and $X_6$ is $C_1$-$C_4$alkyl and the ring B is unsubstituted or substituted by 1 to 4 chlorine atoms.
13. A fluorane compound according to claim 12, wherein $X_5$ and $X_6$ are ethyl or n-butyl.
* * * * *